United States Patent [19]

Yuasa et al.

[11] Patent Number: 5,780,649
[45] Date of Patent: Jul. 14, 1998

[54] PROCESS FOR PREPARING OPTICALLY ACTIVE CYCLIC COMPOUNDS

[75] Inventors: Yoshifumi Yuasa; Masao Konno; Noboru Sano, all of Kanagawa, Japan

[73] Assignee: Takasago International Corporation, Tokyo, Japan

[21] Appl. No.: 706,282

[22] Filed: Sep. 4, 1996

[30] Foreign Application Priority Data

Sep. 8, 1995 [JP] Japan .................. 7-255840

[51] Int. Cl.$^6$ .................. C07D 307/32; C07D 307/02
[52] U.S. Cl. .................. 549/313; 549/475
[58] Field of Search .................. 549/313, 475

[56] References Cited

FOREIGN PATENT DOCUMENTS 6-172256  6/1994  Japan .

OTHER PUBLICATIONS

Chemistry Letters, 1984, pp. 1389–1392, "Combination of Borane–Dimethyl Sulfide Complex with Catalytic Sodium tetrahydroborate as a Selective Reducing . . . Malic Acid".

Database WPI, Week 9429, Derwent Publications Ltd., AN 94-238698.

Tetrahedron Letters, vol. 28, No. 42, 1987, pp. 5033–5036, D. Buisson et al. "New Chiral Building Blocks by Microbial Asymmetric Reduction: A Direct . . . Synthons".

*Primary Examiner*—Amelia Owens
*Attorney, Agent, or Firm*—Sughrue, Mion, Zinn, Macpeak & Seas, PLLC

[57] ABSTRACT

A process for preparing optically active 3-hydroxy-γ-butyrolactone or optically active 3-hydroxytetrahydrofuran through a short route and by using an easily available and inexpensive starting material and an inexpensive reagent easy to handle is disclosed. The process comprises cyclizing an optically active compound represented by formula (II):

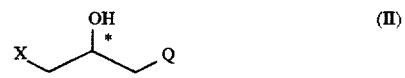

wherein Q represents an alkoxycarbonyl group having 1 to 4 carbon atoms or a hydroxymethyl group; X represents a halogen atom; and the asterisk * means an asymmetric carbon atom, under an acidic condition.

7 Claims, No Drawings

PROCESS FOR PREPARING OPTICALLY ACTIVE CYCLIC COMPOUNDS

FIELD OF THE INVENTION

This invention relates to a novel process for preparing optically active cyclic compounds, more particularly, optically active 3-hydroxy-γ-butyrolactone and optically active 3-hydroxytetrahydrofuran each of which is an useful intermediate for synthesizing pharmaceuticals or agricultural chemicals.

BACKGROUND OF THE INVENTION

Processes for preparing optically active 3-hydroxy-γ-butyrolactone (a compound represented by formula (I) hereinafter shown in which W is a keto group) or optically active 3-hydroxytetrahydrofuran (a compound represented by formula (I) in which W is a methylene group) are known from the literature.

Examples of known processes for preparing optically active 3-hydroxy-γ-butyrolactone include (1) a process comprising 7 steps starting with L-ascorbic acid or D-isoascorbic acid (see Synthesis, pp. 570–572 (1987)), (2) a process comprising diesterifying L-malic acid, reducing the diester using a dimethyl sulfide/borane reagent to form a diol ester, and cyclizing the diol ester using trifluoroacetic acid (see Chemistry Letters, pp. 1389–1392 (1984)), (3) a process comprising 7 steps for converting D-malic acid to 3,4-dihydroxybutanoic acid and cyclizing the 3,4-dihydroxybutanoic acid in the presence of an acid (see Tetrahedron, Vol. 35, pp. 933–940 (1979)), and (4) a process comprising 3 steps starting with L-malic acid (see JP-A-6-172256, the term "JP-A" as used herein means an "unexamined published Japanese patent application").

Known processes for preparing optically active 3-hydroxytetrahydrofuran include (5) a process comprising diesterifying L-malic acid, reducing the diester with lithium aluminum hydride to obtain 1,2,4-butanetriol, and cyclizing the butanetriol in the presence of p-toluenesulfonic acid as a catalyst at a high temperature of about 180° to 220° C. (see J. Org. Chem., Vol. 48, pp. 2767–2769 (1983)).

These known processes, particularly the process (3), are not satisfactory because of involvement of many steps and complicated operations and also in view of yield. The route of the process (4), while relatively short, is not deemed suitable to industrial manufacture because protection with a protective group is required and a silica gel column is used in purification. The reagents used in the processes (2) and (5) are expensive and difficult to handle. Thus, the conventional processes are not accepted as suited to industrial application from the standpoint of economy and efficiency.

SUMMARY OF THE INVENTION

Accordingly, an object of the present invention is to provide an economically and industrially advantageous process for preparing optically active 3-hydroxy-γ-butyrolactone or optically active 3-hydroxytetrahydrofuran through a short route and by using an easily available and inexpensive starting material and an inexpensive reagent easy to handle.

In order to solve the problems associated with the conventional techniques, the inventors of the present invention have extensively studied, seeking for an industrially advantageous process starting with an easily available optically active 4-halo-3-hydroxybutyric ester or optically active 4-halo-1,3-butanediol which is obtained by reducing the optically active 4-halo-3-hydroxybutyric ester. As a result, they have succeeded in cyclizing these starting compounds under an acidic condition to obtain the desired optically active cyclic compounds. The present invention has been completed based on this finding.

The invention provides a novel process for preparing an optically active cyclic compound represented by formula (I):

wherein W represents a keto group (>C=O) when Q in the following formula (II) is a lower alkoxycarbonyl group or W represents a methylene group (—CH₂—) when Q in the following formula (II) is a hydroxymethyl group; and the asterisk * means an asymmetric carbon atom, comprising cyclizing an optically active compound represented by formula (II):

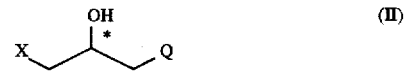

wherein Q represents a lower alkoxycarbonyl group or a hydroxymethyl group; X represents a halogen atom; and the asterisk * means an asymmetric carbon atom, under an acidic condition.

DETAILED DESCRIPTION OF THE INVENTION

In formula (II), the term "lower alkoxycarbonyl group" as used for Q denotes an alkoxycarbonyl group having 1 to 4 carbon atoms in the alkoxy moiety thereof and includes methoxycarbonyl, ethoxycarbonyl, n-propoxycarbonyl, isopropoxycarbonyl, n-butoxycarbonyl, isobutoxycarbonyl, sec-butoxycarbonyl, and t-butoxycarbonyl. The halogen atom as represented by X includes fluorine, chlorine, and bromine.

The term "optically active compound" as used herein is intended to include both an (R)-compound and an (S)-compound.

The optically active compound which can be used as a starting material in the present invention is an optically active 4-halo-3-hydroxybutyric ester of formula (II) in which Q is an alkoxycarbonyl group or an optically active 4-halo-1,3-butanediol of formula (II) in which Q is a hydroxymethyl group.

Of these starting compounds, the optically active 4-halo-3-hydroxybutyric ester can be obtained by, for example, the method disclosed in JP-A-1-211551, which comprises asymmetrically hydrogenating an easily available γ-halogenoacetoacetic ester in the presence of a ruthenium-optically active phosphine complex as a catalyst.

Examples of preferred optically active 4-halo-3-hydroxybutyric esters are ethyl (R)- or (S)-4-chloro-3-hydroxybutyrate, ethyl (R)- or (S)-4-bromo-3-hydroxybutyrate, isopropyl (R)- or (S)-4-chloro-3-hydroxybutyrate, isopropyl (R)- or (S)-4-bromo-3-hydroxybutyrate, t-butyl (R)- or (S)-4-chloro-3-hydroxybutyrate, and t-butyl (R)- or (S)-4-bromo-3-hydroxybutyrate.

Another starting compound for use in the invention, the optically active 4-halo-1,3-butanediol, is obtained by, for example, the method disclosed in JP-A-2-174733, which comprises reducing the above-mentioned 4-halo-3- hydroxybutyric ester using a hydride, such as sodium borohydride, lithium borohydride, lithium aluminum hydride, or diborane.

Examples of preferred optically active 4-halo-1,3-butanediols include (R)- or (S)-4-chloro-1,3-butanediol.

The process of the invention comprises cyclizing the optically active 4-halo-3-hydroxybutyric ester or optically active 4-halo-1,3-butanediol represented by formula (II) under an acidic condition.

That is, the desired optically active cyclic compound of formula (I) can be obtained by adding an aqueous acid solution to the compound of formula (II) and subjecting the compound to cyclization. The acid to be used includes hydrochloric acid, sulfuric acid, hydrobromic acid, hydroiodic acid, and perchloric acid. An aqueous solution of the acid adjusted to a pH of 2.0 or lower, preferably 0.5 to 1.0, is added in an amount 1 to 10 times, preferably 2 to 4 times, the weight of the substrate compound of formula (II); and the reaction mixture is heated at a temperature of 40° to 150° C., preferably 80° to 120° C., for a period of 1 to 10 hours, preferably 2 to 4 hours.

After completion of the reaction, the reaction solution is made neutral with an alkali, e.g., a sodium hydroxide aqueous solution, and water is evaporated under reduced pressure. To the residue is added an organic solvent, such as methyl acetate, ethyl acetate, methanol, ethanol, isopropyl alcohol, diethyl ether, dipropyl ether, acetone, tetrahydrofuran, dioxane, and mixtures thereof, and the insoluble matter precipitated is removed by filtration. The solvent is removed from the filtrate by evaporation under reduced pressure. If necessary, the washing with an organic solvent and the solvent removal are repeated. The residual oily substance is distilled under reduced pressure to give the desired optically active cyclic compound of the invention, i.e., optically active 3-hydroxy-γ-butyrolactone or optically active 3-hydroxytetrahydrofuran.

According to the invention, optically active 3-hydroxy-γ-butyrolactone can be prepared from an industrially available and inexpensive 4-halo-3-hydroxybutyric ester through a single step, and optically active 3-hydroxytetrahydrofuran can be prepared from an optically active 4-halo-1,3-butanediol which is obtained by reducing the optically active 4-halo-3-hydroxybutyric acid. There is no need to protect the hydroxyl group of the starting optically active 4-halo-3-hydroxybutyric ester or optically active 4-halo-1,3-butanediol.

As compared with the conventional processes, the process of the invention is an economical and industrially advantageous process which includes no complicated and troublesome steps.

The invention will now be illustrated in greater detail with reference to Examples and Reference Examples, but it should be understood that the invention is not construed as being limited thereto.

Equipment and instruments used for measurement of physical properties of the products prepared and the conditions of measurement are as follows.

Gas Chromatography:
  5890-II, manufactured by Hewlett Packard;
  Column: Silicone NB-1 (0.25 mm×30 m), manufactured by G. L. Science
  Temp.: raised from 50° C. up to 250° C. at a rate of 10° C./min
Infrared Absorption Spectrum (IR):
  IR-810, manufactured by JASCO Inc.

Mass Spectrum (MS):
  M-80B (ionization potential: 20 eV), manufactured by Hitachi, Ltd.
Nuclear Magnetic Resonance Spectrum (NMR):
  AM-400, manufactured by Bruker Inc.
  $^1$H-NMR: 400 MHz; internal standard: tetramethylsilane
  $^{13}$C-NMR: 100 MHz; internal standard: tetramethylsilane
Optical Rotation:
  DIP-4, manufactured by JASCO Inc.

EXAMPLE 1

Preparation of (S)-3-Hydroxy-γ-butyrolactone

To 500 g (3 mol) of ethyl (S)-4-chloro-3-hydroxybutyrate (produced by Takasago International Corporation; purity: 98%; optical purity: 93% ee) was added 1 l of 0.5N hydrochloric acid, and the solution was heated under reflux for 2 hours. After cooling, the reaction solution was neutralized with a 50% aqueous solution of sodium hydroxide, and water was evaporated under reduced pressure. To the residual mixture of crystals and an oily substance was added 500 ml of ethyl acetate, followed by stirring. The crystals were removed by filtration, and the filtrate was concentrated under reduced pressure. The residue was distilled under reduced pressure to give 232 g of the title compound as a colorless substance (purity: 99%; yield: 75%).
Boiling point: 140° C./1 mmHg
Optical rotation: $[\alpha]_D^{24}$=−79.53° (c=2.07, ethanol)
$^1$H-NMR (CDCl$_3$) δ ppm:
  2.51 (1H, d, J=18 Hz), 2.76 (1H, dd, J=6, 18 Hz), 3.71 (1H, brs, OH), 4.31 (1H, d, J=10.3 Hz), 4.42 (1H, dd, J=4.4, 14.7 Hz), 4.65–4.69 (1H, m, CH—OH)
$^{13}$C-NMR (CDCl$_3$) δ ppm:
  37.81 (CH$_2$), 67.40 (CH), 76.41 (CH$_2$), 177.33 (C=O)
IR $v_{max}$ (neat): 3420, 1775 cm$^{-1}$
MS (m/e, %): 102(2), 74(23), 44(100), 43(60)

EXAMPLE 2

Preparation of (R)-3-Hydroxy-γ-butyrolactone

To 30 g (0.18 mol) of ethyl (R)-4-chloro-3-hydroxybutyrate (produced by Takasago International Corporation; purity: 98%; optical purity: 93% ee) was added 90 ml of 0.5N hydrochloric acid, and the solution was heated under reflux for 2 hours. After cooling, the reaction mixture was neutralized with a 50% aqueous solution of sodium hydroxide, and water was evaporated under reduced pressure. To the residual mixture of crystals and an oily substance was added 50 ml of ethyl acetate, followed by stirring. The crystals were removed by filtration, and the filtrate was concentrated under reduced pressure. The residue was distilled under reduced pressure to give 14.9 g of the title compound as a colorless substance (purity: 96%; yield: 81%).

Optical rotation: $[\alpha]_D^{24}$=+74.73° (c=2.4, ethanol)

EXAMPLE 3

Preparation of (S)-3-Hydroxy-γ-butyrolactone

To 10 g (60 mmol) of ethyl (S)-4-chloro-3-hydroxybutyrate (produced by Takasago International Corporation; purity: 98%; optical purity: 93% ee) was added 20 ml of 0.5N sulfuric acid, and the solution was heated under reflux for 2 hours. After cooling, the reaction mixture was neutralized with a 50% aqueous solution of sodium hydroxide, and water was evaporated under reduced pressure. To the residual mixture of crystals and an oily substance was added 500 ml of ethyl acetate, followed by stirring. The crystals were removed by filtration, and the filtrate was concentrated under reduced pressure. The residue was distilled under reduced pressure to give 5.1 g of the title compound as a colorless substance (yield: 83%).

EXAMPLE 4

Preparation of (S)-3-Hydroxytetrahydrofuran

To 250 g (2 mol) of the (S)-4-chloro-1,3-butanediol obtained in Reference Example 1 hereinafter given was added 500 ml of 0.5N hydrochloric acid, followed by heating under reflux for 2 hours. After cooling, the reaction mixture was neutralized with a 50% aqueous solution of sodium hydroxide, and water was evaporated under reduced pressure. To the residual mixture of crystals and an oily substance was added 500 ml of methanol, followed by stirring. The crystals were removed by filtration, and the filtrate was concentrated under reduced pressure. The residue was distilled under reduced pressure to give 105 g of the title compound as a colorless substance (purity: 99.8%; yield: 68%).

Boiling point: 80° C./11 mmHg

Optical rotation: $[\alpha]_D^{24}$=+16.45° (c=2.45, methanol)

$^1$H-NMR (CDCl$_3$) δ ppm:

1.88–1.92 (1H, m), 2.02–2.09 (1H, m), 3.65 (1H, brs, OH), 3.71–3.85 (2H, m), 3.93–3.97 (1H, m), 4.45–4.48 (1H, m, CH—OH)

$^{13}$C-NMR (CDCl$_3$) δ ppm:

35.28 (CH$_2$), 66.63 (CH$_2$), 71.46 (CH), 75.33 (CH$_2$)

IR $\nu_{max}$ (neat): 3400, 1125 cm$^{-1}$

MS (m/e, %): 88(11), 70(14), 58(61), 57(100), 31(61), 29(75)

EXAMPLE 5

Preparation of (R)-3-Hydroxytetrahydrofuran

To 35 g (0.28 mol) of the (R)-4-chloro-1,3-butanediol obtained in Reference Example 2 hereinafter given was added 70 ml of 0.5N hydrochloric acid, followed by heating under reflux for 2 hours. After cooling, the reaction mixture was neutralized with a 50% aqueous solution of sodium hydroxide, and water was evaporated under reduced pressure. To the residual mixture of crystals and an oily substance was added 60 ml of methanol, followed by stirring. The crystals were removed by filtration, and the filtrate was concentrated under reduced pressure. The residue was distilled under reduced pressure to give 16.6 g of the title compound as a colorless substance (purity: 99.1%; yield: 67%).

Optical rotation: $[\alpha]_D^{23}$=−15.91° (c=2.45, methanol)

EXAMPLE 6

Preparation of (S)-3-Hydroxytetrahydrofuran

To 25 g (0.2 mol) of the (S)-4-chloro-1,3-butanediol obtained in Reference Example 1 hereinafter given was added 50 ml of 0.5N sulfuric acid, followed by heating under reflux for 2 hours. After cooling, the reaction mixture was neutralized with a 50% aqueous solution of sodium hydroxide, and water was evaporated under reduced pressure. To the residual mixture of crystals and an oily substance was added 50 ml of methanol, followed by stirring. The crystals were removed by filtration, and the filtrate was concentrated under reduced pressure. The residue was distilled under reduced pressure to give 11.6 g of the title compound as a colorless substance (yield: 66%).

REFERENCE EXAMPLE 1

Preparation of (S)-4-Chloro-1,3-butanediol

To 2 l of tetrahydrofuran was added 114 g (3 mol) of sodium borohydride, and the mixture was heated under reflux. To the mixture was added dropwise a solution of 500 g (3 mol) of ethyl (S)-4-chloro-3-hydroxybutyrate (produced by Takasago International Corporation; purity: 98%; optical purity: 93% ee) in 800 ml of tetrahydrofuran over a 2 hour period. After the addition, the mixture was further heat-refluxed for 1 hour, followed by cooling. The solvent was recovered under reduced pressure, and to the residue was added 1 l of 4N hydrochloric acid while stirring under cooling. The reaction mixture was extracted with 1 l of ethyl acetate, and the extract was neutralized with a 10% aqueous solution of sodium carbonate and washed twice with a 10% aqueous solution of sodium chloride. The organic layer was dried over anhydrous magnesium sulfate, and the solvent was recovered under reduced pressure to give 320 g of the title compound as an oily substance (yield: 86%).

Optical rotation: $[\alpha]_D^{24}$=−23.31° (c=1.1, methanol)

$^1$H-NMR (CDCl$_3$) δ ppm:

1.72–1.88 (2H, m), 2.87 (2H, brs, OH), 3.54 (1H, dd, J=6.7, 11.2 Hz), 3.62 (1H, dd, J=4.4, 11.2 Hz), 3.79–3.92 (2H, m), 4.02–4.11 (1H, m)

IR $\nu_{max}$ (neat): 3350 cm$^{-1}$

REFERENCE EXAMPLE 2

Preparation of (R)-4-Chloro-1,3-butanediol

To 400 ml of tetrahydrofuran was added 23 g (0.6 mol) of sodium borohydride, followed by heat-refluxing. To the mixture was added dropwise a solution of 100 g (0.6 mol) of ethyl (R)-4-chloro-3-hydroxybutyrate (produced by Takasago International Corporation; purity: 98%; optical purity: 93% ee) in 400 ml of tetrahydrofuran over a period of 2 hours, followed by heating under reflux for 1 hour. After cooling, the solvent was recovered under reduced pressure, and to the residue was added 200 ml of 4N hydrochloric acid while cooling and stirring. The reaction mixture was extracted with 300 ml of ethyl acetate, and the extract was neutralized with a 10% aqueous solution of sodium carbonate and washed twice with a 10% aqueous solution of sodium chloride. The organic layer was dried over anhydrous magnesium sulfate, and the solvent was recovered under reduced pressure to give 65 g of the title compound as an oily substance (yield: 87%).

Optical rotation: $[\alpha]_D^{24}$=+23.54° (c=1.2, methanol)

While the invention has been described in detail and with reference to specific examples thereof, it will be apparent to one skilled in the art that various changes and modifications can be made therein without departing from the spirit and scope thereof.

What is claimed is:

1. A process for preparing an optically active cyclic compound represented by formula (I):

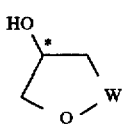

(I)

wherein W represents a keto group when Q in the following formula (II) is a lower alkoxycarbonyl group or W represents a methylene group when Q in the following formula (II) is a hydroxymethyl group; and the asterisk * means an asymmetric carbon atom,
comprising cyclizing an optically active compound represented by formula (II):

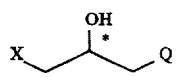

(II)

wherein Q represents a lower alkoxycarbonyl group or a hydroxymethyl group; X represents a halogen atom; and the asterisk * means an asymmetric carbon atom, wherein said cyclizing is conducted by adding an aqueous acid solution to the compound of formula (II) and subjecting the compound of formula (II) to cyclization under an acidic condition, wherein the aqueous acid solution has a pH of 2.0 or lower and is added in an amount 1 to 10 times the weight of the compound of formula (II).

2. The process for preparing an optically active cyclic compound as in claim 1, wherein the lower alkoxycarbonyl group represented by Q in formula (II) is an alkoxycarbonyl group having 1 to 4 carbon atoms in the alkoxy moiety thereof.

3. The process for preparing an optically active cyclic compound as in claim 1, wherein the halogen atom represented by X in formula (II) is fluorine atom, chlorine atom, or bromine atom.

4. The process for preparing an optically active cyclic compound as in claim 1, wherein the acid to be used for the aqueous acid solution is selected from the group consisting of hydrochloric acid, sulfuric acid, hydrobromic acid, hydroiodic acid, and perchloric acid.

5. The process for preparing an optically active cyclic compound as in claim 1, wherein the cyclization is conducted at a temperature of 40° to 150° C. for a period of 1 to 10 hours.

6. The process for preparing an optically active cyclic compound as in claim 1, wherein the aqueous acid solution has a pH of 0.5 to 1.0.

7. The process for preparing an optically active cyclic compound as in claim 6, wherein the aqueous acid solution is added in an amount of 2 to 4 times the weight of the compound of formula (II).

* * * * *